US008017327B2

(12) United States Patent
Wang et al.

(10) Patent No.: US 8,017,327 B2
(45) Date of Patent: Sep. 13, 2011

(54) SINGLE NUCLEOTIDE POLYMORPHISM GENOTYPING DETECTION VIA THE REAL-TIME INVADER ASSAY MICROARRAY PLATFORM

(75) Inventors: Wendy Wang, Shanghai (CN); Zhenhong Sun, Shanghai (CN); Tao Pan, Shanghai (CN); Xuanbin Liu, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 255 days.

(21) Appl. No.: 12/257,026

(22) Filed: Oct. 23, 2008

(65) Prior Publication Data

US 2010/0105575 A1    Apr. 29, 2010

(51) Int. Cl.
*C12Q 1/68* (2006.01)
(52) U.S. Cl. .......................................... 435/6
(58) Field of Classification Search ............... None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,965,188 | A | 10/1990 | Mullis et al. |
| 2006/0088844 | A1 | 4/2006 | Xu |

FOREIGN PATENT DOCUMENTS

| WO | WO-03/089654 A2 | 10/2003 |
| WO | WO-2005/068660 A1 | 7/2005 |
| WO | WO-2006/079049 A2 | 7/2006 |
| WO | WO-2008080254 | 7/2008 |
| WO | WO-2008092291 | 8/2008 |

OTHER PUBLICATIONS

"European Application Serial No. 09173856.7, European Search Report mailed Mar. 10, 2010", 4 pgs.
Breen, G., "Novel and alternative SNP and genetic technologies", *Psychiatric Genetics*, 12(2), (2002), 83-88.
Olivier, M., "The Invader® assay for SNP genotyping", *Mutation Research*, 573(1-2), (2005), 103-110.
"European Application Serial No. 09173856.7, Office Action mailed Apr. 6, 2010", 4 Pgs.
"European Application Serial No. 09173856.7, Response filed Aug. 13, 2010 to Communication dated Apr. 6, 2010", 11 pgs.
"European Application No. 09173856.7, Response filed Apr. 19, 2011 to Office Action mailed Dec. 15, 2010", 10 pgs.

*Primary Examiner* — James Martinell
(74) *Attorney, Agent, or Firm* — Schwegman, Lundberg & Woessner P.A.

(57) ABSTRACT

A method and apparatus for real-time, simultaneous, quantitative measurement for detecting a single nucleotide polymorphism in a target nucleic acid is provided. This method involves combining a polymerase chain reaction (PCR) technique with invader assay technique.

12 Claims, 6 Drawing Sheets

SINGLE NUCLEOTIDE POLYMORPHISM GENOTYPING DETECTION VIA THE REAL-TIME INVADER ASSAY MICROARRAY PLATFORM

BACKGROUND OF THE INVENTION

The most common type of genetic variation is single nucleotide polymorphism (SNP), which may include polymorphism in both DNA and RNA a position at which two or more alternative bases occur at appreciable frequency in the people population (>1%). Base variations with the frequency <1% are called point mutations. For example, two DNA fragments in the same gene of two individuals may contain a difference (e.g., AAGTACCTA to AAGTGCCTA) in a single nucleotide to form a single nucleotide polymorphism (SNP). Typically, there exist many single nucleotide polymorphism (SNP) positions (about $1/1000^{th}$ chance in whole genome) in a creature's genome. As a result, single nucleotide polymorphism (SNP) and point mutations represent the largest source of diversity in the genome of organisms, for example, a human.

Most single nucleotide polymorphisms (SNP) and point mutations are not responsible for a disease state. Instead, they serve as biological markers for locating a disease on the human genome map because they are usually located near a gene associated with a certain disease. However, many mutations have been directly linked to human disease and genetic disorder including, for example, Factor V Leiden mutations, hereditary haemochromatosis gene mutations, cystic fibrosis mutations, Tay-Sachs disease mutations, and human chemokine receptor mutations. As a result, detection of single nucleotide polymorphisms (SNPs) and similar mutations are of great importance to clinical activities, human health, and control of genetic disease.

Neutral variations are important, for example, because they can provide guideposts in the preparation of detailed maps of the human genome, patient targeted drug prescription, and identify genes responsible for complex disorder. Moreover, since genetic mutation of other species (e.g., bacteria, viruses, etc.) can also be regarded as a type of single nucleotide polymorphism (SNP), the detection of single nucleotide polymorphism (SNP) can also be used to diagnosis the drug resistance, phenotype/genotype, variants and other information of microorganisms that may be useful in clinical, biological, industrial, and other applications.

There are several methods for detecting single nucleotide polymorphism (SNP) and mutations. The invader assay method is a sensitive method for single nucleotide polymorphism detection and quantitative determination of viral load and gene expression. In the basic invader assay, two synthetic oligonucleotides, the invasive and signal probes, anneal in tandem to the target strand to form the overlapping complex, which may be recognized by a flap endonuclease (FEN).

However, most of the methods are not suitable to be adapted to the platform of automated high-throughput assays or to multiplex screening.

BRIEF DESCRIPTION OF THE DRAWINGS

Embodiments of the invention may be best understood by referring to the following description and accompanying drawings, which illustrate such embodiments. In the drawings.

DETAILED DESCRIPTION OF THE INVENTION

The present invention provides a method and an apparatus for determining the highly sensitive multiplex single nucleotide polymorphism and mutation detection using a real time invader assay microarray platform. This method may be used for real time analysis in which the polymerase chain reaction (PCR) method may be used to generate amplified nucleic acid products to the detectable level in a short time, typically less than 2 hours. As a result, the method is suitable for the real time analysis. This method is also very sensitive. For example, the structure-specific cleavage is highly sensitive to sequence mismatches and uses flap endonuclease (FEN) activity to detect the single nucleotide polymorphism (SNP) in a target nucleic acid. This method is a quantitative assay of the specific target in the sample. The method is a simple operation, which allows for an integrated design to eliminate the transfer step after the polymerase chain reaction (PCR) and wash step after the invader single nucleotide polymorphism (SNP) assay. The method affords minimum cross-contamination because the polymerase chain reaction (PCR) and single nucleotide polymorphism (SNP) assay are performed in the integrated, airtight chamber. As a result, the amplified nucleic acid of different templates would not cross-contaminate each other. Further, the method poses very little biosafety hazard and reduces the chemical disposal related issues by using a closed reaction chamber.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993 and *Hawley's Condensed Chemical Dictionary*, $14^{th}$ edition, Wiley Europe, 2002.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the term "buffer solution" refers to a solution that resists changes in the pH. A suitable reaction buffer for a microarray is described in PCT Patent Application Publication No. WO 2008/080254.

As used herein, the term "evanescent" refers to a nearfield standing wave exhibiting exponential decay with distance. A suitable evanescent wave system that may be used in the practice of this invention is described, for example, in U.S. Patent Application Publication No. 2006/0088844. A suitable microarray reader based on evanescent wave is described in PCT Patent Application Publication No. WO 2008/092291.

As used herein, the term "flap endonuclease (FEN)" refers to a type of nucleolytic enzyme that acts as both as a 5'-3' exonuclease and a structure specific endonuclease on specialized DNA structures that occur during the biological processes of DNA replication, DNA repair, and DNA recombination.

As used herein, the term "hybridization" refers to the pairing of complementary nucleic acids.

As used herein, the term "invader assay" refers to an assay method in which a structure-specific flap endonuclease (FEN) cleaves a three-dimensional complex formed by hybridization of allele-specific overlapping oligonucleotides to target DNA containing a single nucleotide polymorphism (SNP) site.

As used herein, the term "invader probe" refers to an oligonucleotide that is complementary to the target sequence 3' of the polymorphic site and ends with a non-matching base overlapping the single nucleotide polymorphism (SNP) nucleotide; it can either be tethered onto a solid phase carrier or in a reaction solution.

As used herein, the term "linker" refers to a carbon chain, which may include other elements that covalently attaches two chemical groups together.

As used herein, the term "microarray" is a linear or two-dimensional microarray of discrete regions, each having a defined area, formed on the surface of a solid support.

As used herein, the term "nucleic acid" refers to any nucleic acid containing molecule including, but not limited to, DNA or RNA.

As used herein, the term "nucleic acid sequence" refers to an oligonucleotide, nucleotide or polynucleotide, and fragments or portions thereof, and to DNA or RNA of genomic or synthetic origin which may be single or double stranded, and represent the sense or antisense strand.

As used herein, the term "polymerase chain reaction (PCR)" refers to the method of K. B. Mullis, U.S. Pat. Nos. 4,683,195, 4,683,202, and 4,965,188.

As used herein, the term "primer" refers to a single-stranded polynucleotide capable of acting as a point of initiation of template-directed DNA synthesis under appropriate conditions.

As used herein, the term "probe" refers to a nucleic acid capable of binding to a target nucleic acid of complementary sequence through one or more types of chemical bonds, usually through complementary base pairing, usually through hydrogen bond formation, thus forming a duplex structure.

As used herein, the term "sequence variation" refers to differences in nucleic acid sequence between two nucleic acids.

As used herein, the term "single nucleotide polymorphism (SNP)" refers to a DNA sequence variation occurring when a single nucleotide—A, T, C, or G—in the genome (or other shared sequence) differs between members of a species (or between paired chromosomes in an individual).

As used herein, the term "signal probe" refers to a DNA sequence which may be cleaved by the enzyme at the site of its overlap with the 3' end of the invasive probe. This cleavage releases the noncomplementary 5' flap of the signal probe plus one nucleotide of its target-specific region. The cleaved 5' flap serves as a signal for the presence, and enables quantitative analysis, of the specific target in the sample. The signal probe is tethered onto the solid phase carrier.

As used herein, the term "substrate" refers to material capable of supporting associated assay components (e.g., assay regions, cells, test compounds, etc.).

As used herein, the term "target nucleic acid" refers to a polynucleotide. The polynucleotide is genetic material including, for example, DNA/RNA, mitochondrial DNA, rRNA, tRNA, mRNA, viral RNA, and plasmid DNA.

As used herein, the term "thermostable" refers to an enzyme, such as a 5' nuclease, indicates that the enzyme is functional or active (i.e., can perform catalysis) at an elevated temperature, for example, at about 55° C. or higher.

As used herein, the term "melting temperature ($T_m$)" refers to the temperature at which a population of double-stranded nucleic acid molecules becomes half dissociated into single strands.

The present invention provides a quantitative method for detecting a single nucleotide polymorphism in a target nucleic acid. The method includes: (a) providing an amplified target nucleic acid suspected of having a single polynucleotide polymorphism, wherein a target nucleic acid is amplified by a polymerase chain reaction; (b) annealing an invader probe and a signal probe to a single-strand of the amplified target nucleic acid suspected of having a single polynucleotide polymorphism to provide a sample complex, wherein the invader probe includes sequences selected to anneal to the single-strand of the amplified target nucleic acid 5' to the single polynucleotide polymorphism and a 3' most nucleotide that does not anneal to the single polynucleotide polymorphism, wherein the signal probe includes a fluorescent label linked to sequences selected to not anneal to the single-strand of the amplified target nucleic acid or to the invader probe linked to sequences selected to anneal to the target nucleic acid with a single nucleotide polymorphism, wherein the signal probe includes a fluorescence quencher linked to sequences selected to anneal to the single-strand of the amplified target nucleic acid or to the invader probe linked to sequences selected to anneal to the single-strand of the amplified target nucleic acid suspected of having a single polynucleotide polymorphism; (c) contacting the sample complex with a flap endonuclease to activate a fluorescence response; wherein if the signal probe anneals to the single-strand of the amplified target nucleic acid at a single polymorphic nucleotide, the flap endonuclease cleaves the signal probe 3' to the single polymorphic nucleotide producing a cleaved 5' flap sequence that produces the fluorescent response; and (d) detecting the fluorescence response.

In one embodiment, the providing an amplified target nucleic acid suspected of having a single polynucleotide polymorphism includes: (i) denaturing the target nucleic acid to provide a pair of single-stranded target nucleic acids; (ii) annealing a primer to the each single-stranded target nucleic acid; and (iii) extending each primer annealed to each single-stranded target nucleic acid to provide an amplified target nucleic acid. In another embodiment, the method further includes analyzing the fluorescence response.

In one embodiment, the signal probe is immobilized on an upper surface of a substrate or both the signal probe and the invader probe are immobilized on an upper surface of a substrate.

The present invention provides another quantitative method for detecting a single nucleotide polymorphism in a target nucleic acid. The method includes: (a) providing an amplified target nucleic acid suspected of having a single polynucleotide polymorphism, wherein a target nucleic acid is amplified by a polymerase chain reaction; (b) annealing an invader probe and a signal probe to a single-strand of the amplified target nucleic acid suspected of having a single polynucleotide polymorphism to provide a sample complex, wherein the invader probe includes sequences selected to anneal to the single-strand of the amplified target nucleic acid 5' to the single polynucleotide polymorphism and a 3' most nucleotide that does not anneal to the single polynucleotide polymorphism; wherein the signal probe includes sequences selected to not anneal to the single-strand of the amplified target nucleic acid or to the invader probe linked to sequences selected to anneal to the target nucleic acid with a single nucleotide polymorphism; (c) contacting the sample complex with a flap endonuclease to provide a 5' flap sequence, wherein if the signal probe anneals to single-strand of the amplified target nucleic acid at a single polymorphic nucleotide, the flap endonuclease cleaves the signal probe 3' to the single polymorphic nucleotide to provide the 5' flap sequence;(d) annealing the 5' flap sequence to a probe immobilized on an upper surface of a substrate, wherein the probe includes a nucleotide sequence that is complementary to the 5' flap sequence and to a fluorescent energy transfer cassette positioned a 5' end of the probe and includes a fluorophore and a fluorescence quencher;(e) cleaving the fluorescent energy transfer cassette between the fluorophore and the fluorescence quencher with a flap endonuclease to activate a fluorescence response; and (f) detecting the fluorescence response.

In one embodiment, the providing an amplified target nucleic acid suspected of having a single polynucleotide polymorphism includes: (i) denaturing the target nucleic acid to provide a pair of single-stranded target nucleic acids; (ii) annealing a primer to the each single-stranded target nucleic acid; and (iii) extending each primer annealed to each single-stranded target nucleic acid to provide an amplified target nucleic acid. In another embodiment, the method further includes analyzing the fluorescence response.

In one embodiment, the probe is printed and immobilized onto the substrate using a micro-array printer. In another embodiment, the substrate includes silicon, glass, quartz, a ceramic, a rubber, a metal, a polymer, a hybridization membrane, or a combination thereof. In yet another embodiment, the substrate is chemically modified with a reagent selected from a silane, avidin, poly-L-lysine, streptavidin, a polysaccharide, a mercaptan, or a combination thereof.

In one embodiment, the probe includes a linker with a sulfhydryl (RSH), amino ($NH_2$), hydroxyl (OH), carboxaldehyde (CHO), or carboxylic acid (COOH) group at the 3' end. In another embodiment, the linker includes about a ten nucleotide random oligomer. In yet another embodiment, the probe is immobilized onto a silanized glass substrate with the sulfhydryl (RSH) group at the 3' end.

The present invention further provides an apparatus. The apparatus includes: a closed reactor including: a substrate having opposing first and second planar opposing surfaces, the substrate having a cavity and a refractive index greater than a refractive index of water; a buffer layer arranged over the first planar surface of the substrate; a cover plate arranged over the buffer layer and the cavity, the cover plate in combination with the cavity and buffer layer defining a reaction chamber; and at least one inlet port and at least one outlet port to communicate with the reaction chamber through the substrate to enable the passage of fluid from an external source into and through the reaction chamber; a temperature control system coupled to the closed reactor to cycle the temperature of a buffer solution contained within the closed reactor, wherein the buffer solution is substantially in contact with the first surface of the substrate and being capable of sustaining a plurality of polymerase chain reactions, a plurality of hybridization reactions, containing one or more primers, one or more dNTPs, a target nucleic acid suspected of having a single polynucleotide polymorphism, a signal probe, an invader probe, and a flap endonuclease; a light source coupled to the closed reactor to provide a ray of light having a wavelength chosen to activate a fluorophore immobilized on the first surface of the substrate, incident on an interface between the substrate and the buffer solution at an angle chosen to propagate an evanescent wave into the buffer solution; and a detector coupled to the closed reactor to detect a fluorescent response.

In one embodiment, the detector is mobile and capable of sequentially detecting fluorescent light emitted by the fluorophore. In another embodiment, the closed reactor is mobile and capable of being sequentially addressed by the detector. In yet another embodiment, the detector includes a camera, a charge-coupled device, a charge-injection device, a complementary metal-oxide-semiconductor (CMOS) device, a video camera, a silicon photo-cell, a photodiode, an avalanche photodiode, a photo-multiplier tube, or a combination thereof.

Figure 1:
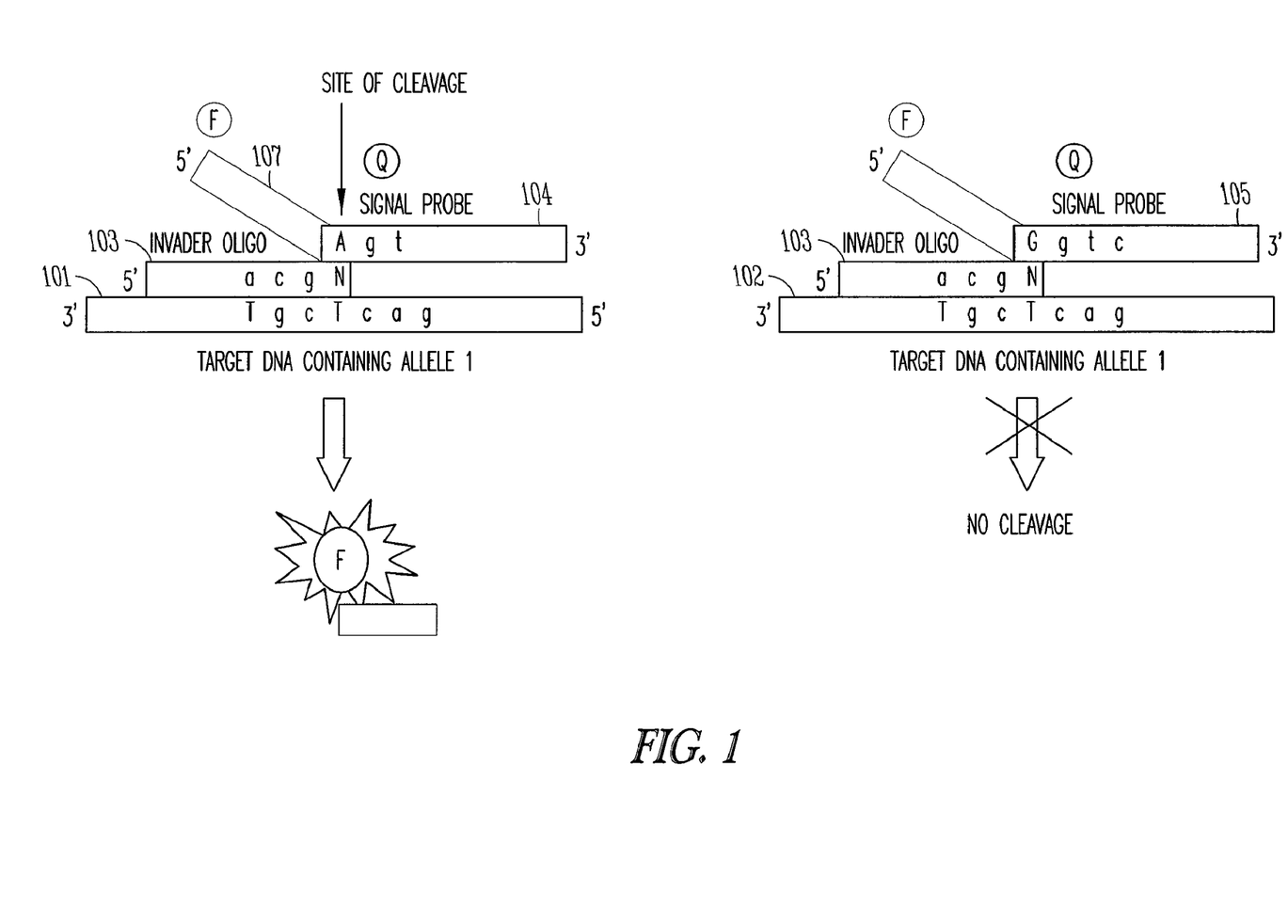
FIG. 1 illustrates an exemplary single nucleotide polymorphism (SNP) invader assay mechanism.

FIG. 1 illustrates an exemplary single nucleotide polymorphism (SNP) invader assay mechanism. The invader assay is a sensitive method for single nucleotide polymorphism detection and also for quantitative determination of viral load and gene expression. In the basic invader assay, two synthetic oligonucleotides (101,102), the invader probe (103) and signal probes (104,105), anneal in tandem to the target strand to form an overlapping complex, which can be recognized by a flap endonuclease (FEN). The invader probe (103) includes a nucleotide, which in this example, is not A. The flap endonuclease (FEN) cleaves the signal probe (104) at the site of its overlap with the 3' end of the invader probe (103). This cleavage releases the noncomplementary 5' flap (107) of the signal probe (104) plus one nucleotide of its target-specific region. The cleaved 5' flap (107) serves as a signal for the presence, and enables quantitative analysis, of the specific target in the sample.

Figure 2:
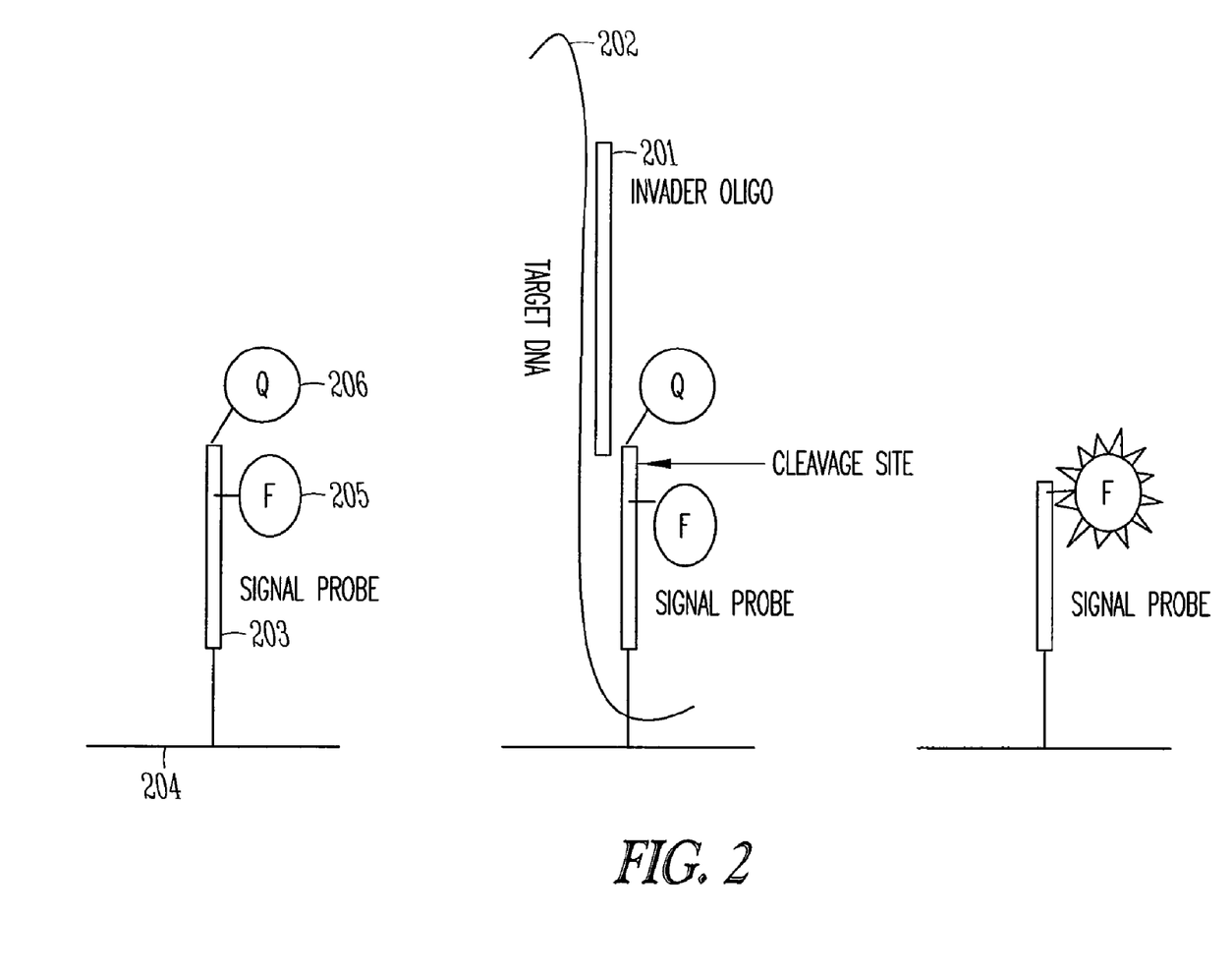
FIG. 2 illustrates an exemplary monoplex solid-phase invasive cleavage reaction.

FIG. 2 illustrates an exemplary monoplex solid-phase invasive cleavage reaction in which an invader probe (201) for each array location is added to the reaction with a target nucleic acid (202) and flap endonuclease (FEN). If the target nucleic acid probe (203), which is attached to the substrate (204), is designed as a fluorescence resonance energy transfer (FRET) molecule containing a fluorophore (205) at the 5'-end and an internal quencher molecule (206), the cleavage reaction separates the fluorophore (205) from the quencher (206) and generates a measurable fluorescent signal.

Figure 3:
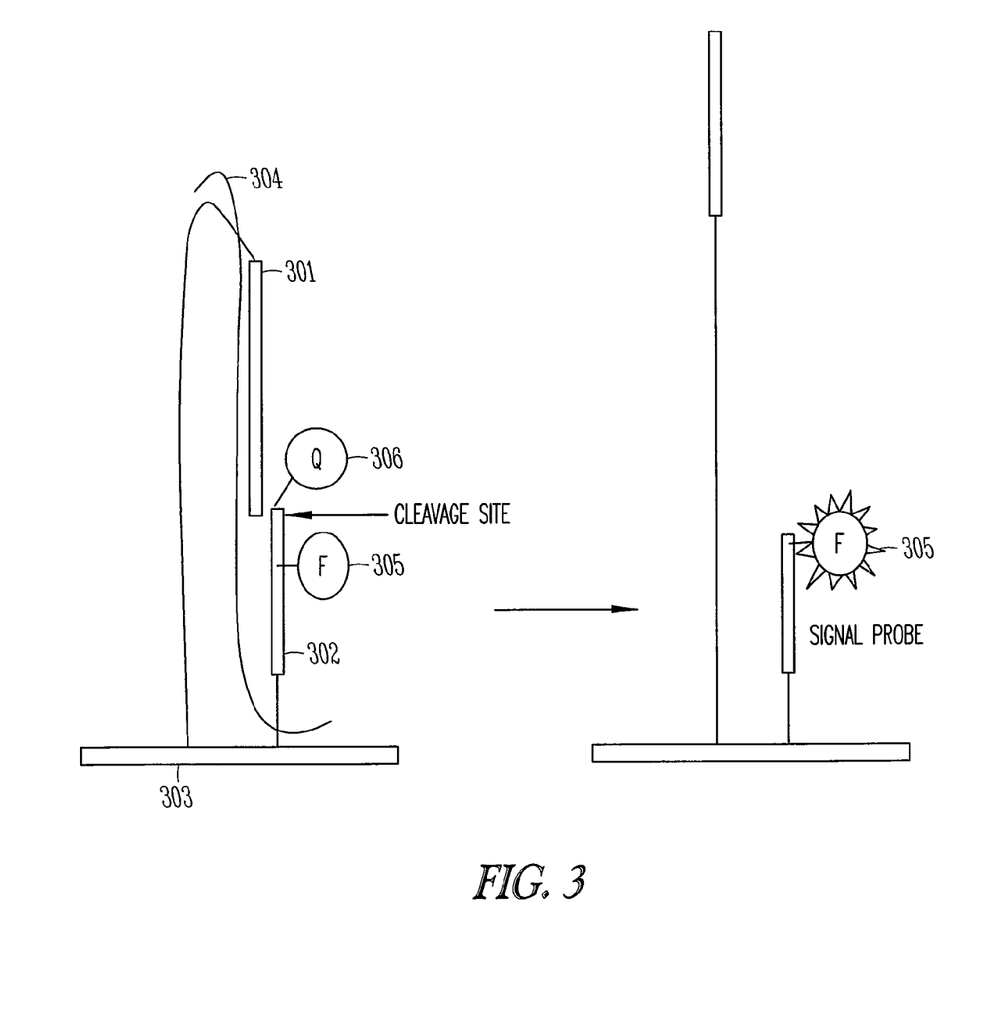
FIG. 3 illustrates another exemplary monoplex solid-phase invasive cleavage reaction.

FIG. 3 illustrates another exemplary monoplex solid-phase invasive cleavage reaction in which an invader probe (301) and a target nucleic acid probe (302) are tethered to the solid phase (303), so that only a sample (304) and flap endonuclease (FEN) are added for array processing.

Figure 4:
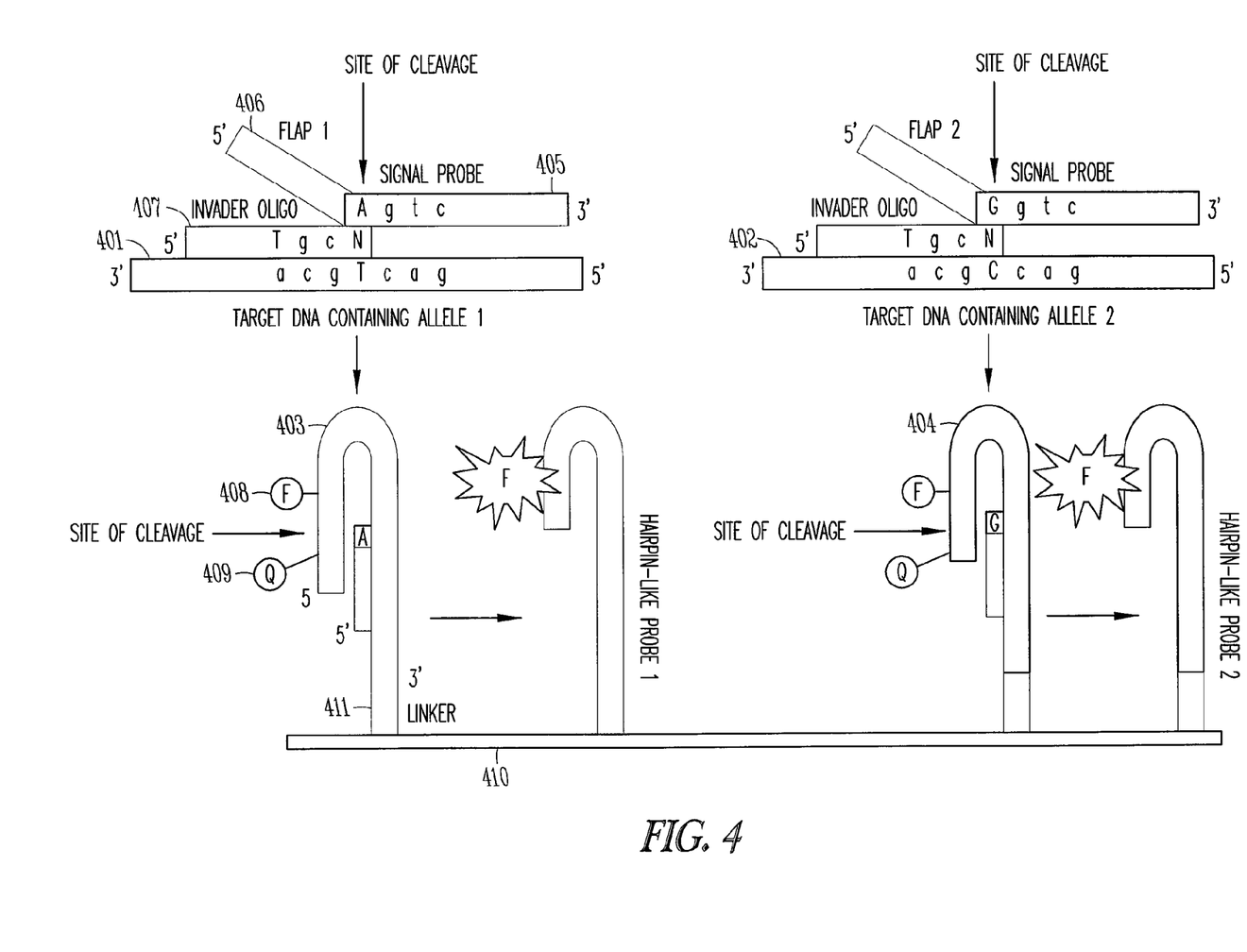
FIG. 4 illustrates an exemplary biplex solid-phase invasive cleavage reaction.

FIG. 4 illustrates an exemplary biplex solid-phase invasive cleavage reaction in which different alleles (401, 402) may be detected by different hairpin-like probes (403, 404), respectively. For example, a signal probe may have two regions: a target-specific region (405) and a 5' flap region (406). The target-specific region (405) of each signal probe may be complementary to the target sequence (401 or 402) and the melting temperature of the signal probe-target duplex may be close to the assay temperature. The 5' flap region (406) of the signal probe may be non-complementary to both the target (401 and/or 402) and the invader probe (407) sequence. The 5' flap region (406) of the signal probe may serve as a signal for the presence of the target nucleic acids (401 and/or 402) to enable the quantitative analysis of the single nucleotide polymorphism (SNP). Further, the 5' flap region (406) of the signal probe may be designed to anneal to the hairpin-like immobilized probe (403 and/or 404) on the surface facing the fluorophore and the quencher at the assay temperature.

An invader probe (407) may be complementary to the target nucleic acid sequence 3' to the polymorphic site and ends with a non-matching base, which overlaps the single nucleotide polymorphism (SNP) nucleotide. An invader probe (407) may be designed to anneal to the target DNA (401 and/or 402) at the assay temperature.

A target nucleic acid probe (403 and/or 404) may be a hairpin-like immobilized probe. A hairpin-like immobilized target nucleic acid probe may contain a signal dye molecule (408) (e.g., fluorophore) and a quencher dye molecule (409) pair, i.e., a fluorescence resonance energy transfer (FRET) cassette. Cleavage of the fluorescence resonance energy transfer (FRET) cassette releases the signal dye molecule (408) (e.g., fluorophore), which produces a fluorescent signal when it is separated from the quencher (409). The hairpin-like immobilized target nucleic acid probe may be arrayed and tethered on the solid phase carrier (410) by the linker (411).

For example, if probe 2 matches the single nucleotide polymorphism (SNP) allele present in the target DNA, the hairpin-like probe 2 located in another array position, which has sequences complementary to those in probe 2, is cleaved and generates fluorescence in the other array position. This distinction is highly specific with only minimal unspecific cleavage of the mismatch probe. Each flap sequence is specific for one FRET cassette molecule, and thus generates a distinct fluorescent signal.

To employ an invader assay on a microarray, the hairpin-like synthetic oligonucleotides (403) are immobilized on a glass slide surface (410) via a chemical linker (411) and are present in an excess quantity. The invader probe (407) may be designed to anneal to the target DNA (401), and the cleaved 5' flap (406) may be designed to anneal to the hairpin-like immobilized probe (403) at the assay temperature. In contrast, the signal probe (405) may be designed to have a melting temperature of the assay temperature. During annealing of the cleaved 5' flap (406) to the hairpin-like immobilized probe (403), an enzyme can cleaves the fluorescence resonance energy transfer (FRET) cassette, the quencher (409) detaches, and a fluorescence signal may be produced. The fluorescent signal may be excited by the laser and captured by the charge-coupled device (CCD), as shown in FIG. 5.

Figure 5:
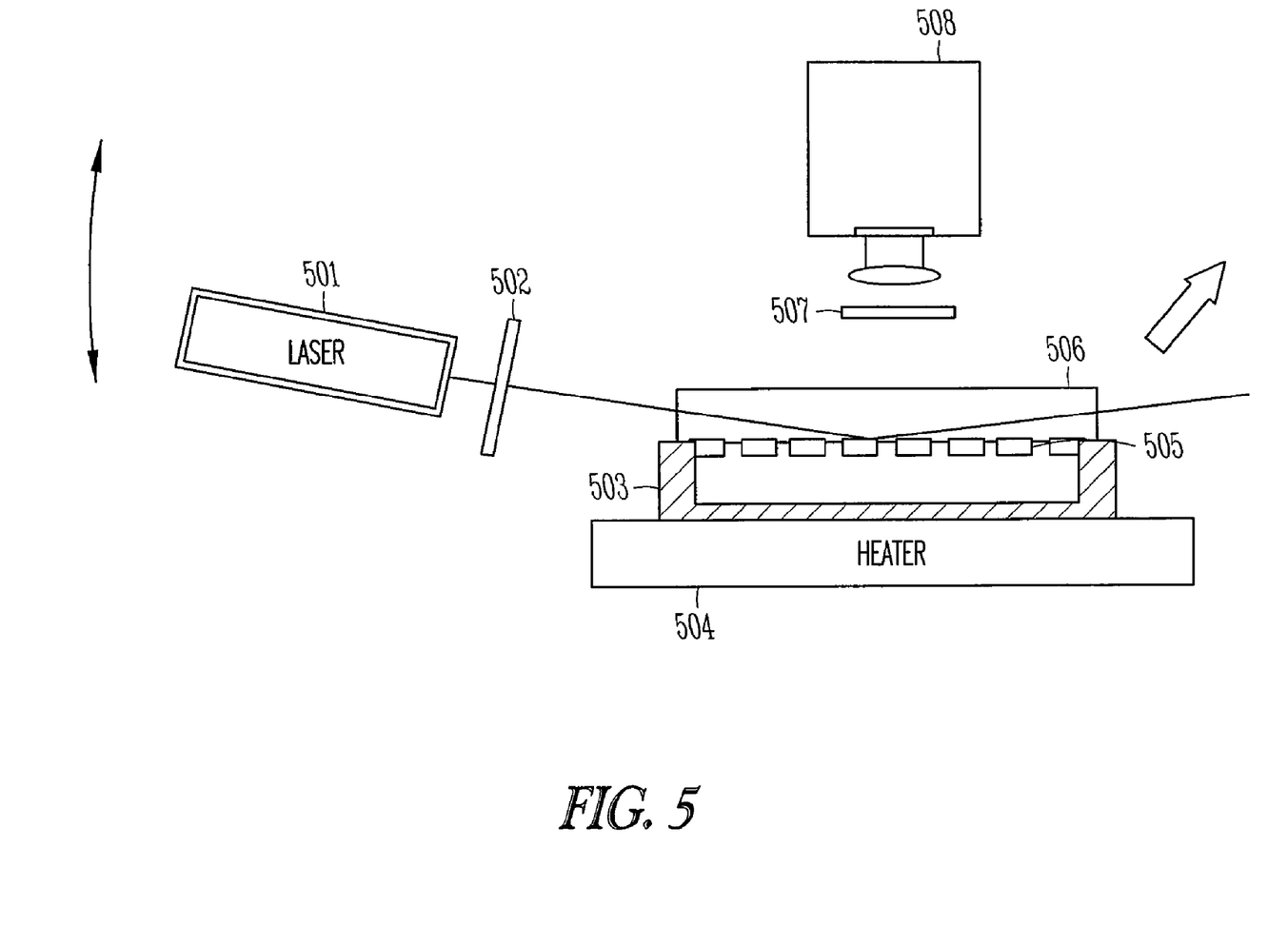
FIG. 5 illustrates an exemplary instrumentation configuration and chip design.

FIG. 5 illustrates an exemplary instrumentation configuration and chip design. The configuration includes, for example, a laser (501), a shutter (502), a chamber (503), a heater (504), probes (505), a solid phase carrier (506), a lens (507) and a detector (508). In one embodiment, the polymerase chain reaction (PCR) and invader assay reaction are performed in the same chamber (503). The instrumentation may detect the single nucleotide polymorphism (SNP) by the invader assay method after each polymerase chain reaction (PCR) cycle, or detect the single nucleotide polymorphism (SNP) after the polymerase chain reaction (PCR) cycles generate sufficient nucleic acid. The solid phase carrier (506) may be transparent and be able to be chemically modified. Suitable solid phase carriers include, for example, glass and plastic. The probes (505) of single nucleotide polymorphism (SNP) array are tethered onto the solid phase carrier (506). In this embodiment, a laser (501) may be used to excite the fluorescent signals of the cleaved probes while a detector (508) may be used capture the fluorescent signals. In one embodiment, the evanescent field of the laser light is a non-transverse wave having components in all spatial orientations, decreasing in field intensity with penetration into medium of n2.

Figure 6:
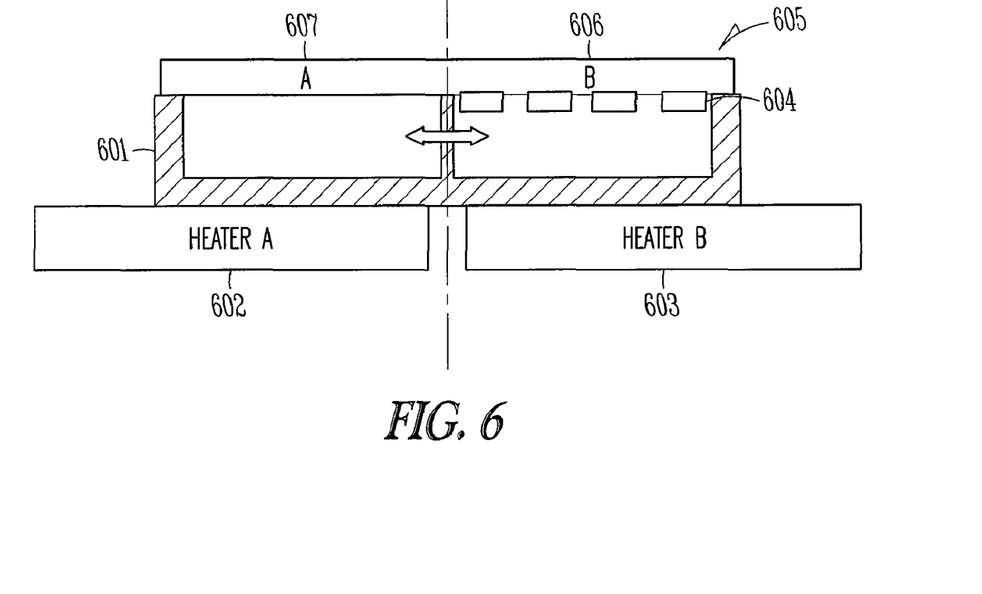
FIG. 6 illustrates a second exemplary chip design.

FIG. 6 illustrates another exemplary chip design. This chip design includes, for example, a biochip (601), a Heater A (602), a Heater B (603), probes (604), a solid phase carrier (605), a single nucleotide polymorphism (SNP) assay chamber (606), and a polymerase chain reaction (PCR) chamber (607). In one embodiment, the biochip (601) includes a single nucleotide polymorphism (SNP) assay reaction chamber (606) and a polymerase chain reaction chamber (607), which are in mutual contact by fluid channels. The fluid may be moved through the channels (not shown) from the polymerase chain reaction (PCR) chamber (607) to the single nucleotide polymorphism (SNP) assay chamber (606) after the polymerase chain reaction (PCR) process is accomplished. In one embodiment, Heater A (602) controls the polymerase chain reaction (PCR) temperature cycles for the polymerase chain reaction (PCR) chamber (607), for example, cycling the temperature of the fluid from 90° C. to 60° C. to 72° C. Heater B (603) controls the single nucleotide polymorphism (SNP) assay temperature for the single nucleotide polymorphism (SNP) assay chamber (606), for example, holding the temperature of chamber (606) at 64° C.

Figure 7:
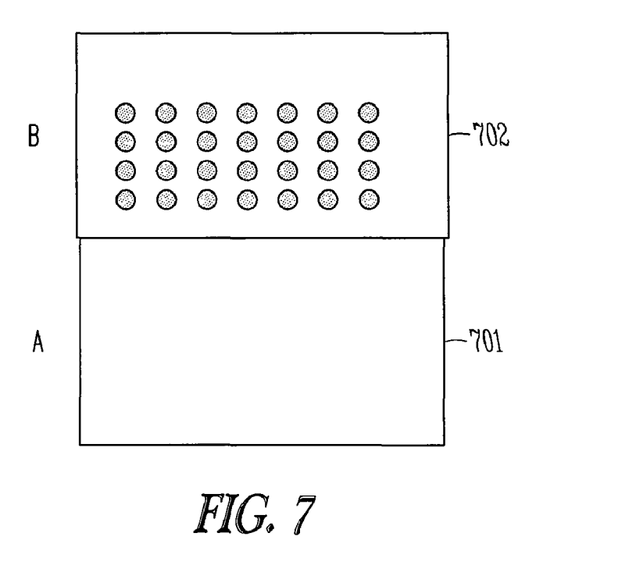
FIG. 7 illustrates an exemplary solid phase carrier.

FIG. 7 illustrates an exemplary solid phase carrier. In one embodiment, the solid phase carrier (701) may be transparent and capable of chemical modification. Suitable solid phase carriers include, for example, glass and plastic. The probes (702) of the single nucleotide polymorphism (SNP) array are tethered onto the solid phase carrier (701).

An example of the highly sensitive multiplex single nucleotide polymorphism and mutation detection using a real time invader assay microarray platform is given below. For example, genes involved in blood pressure regulation in humans may be analyzed. The first single nucleotide polymorphism (SNP), CD36, is located in exon 14 past the stop codon in the gene. The second single nucleotide polymorphism (SNP), PTP03, is a synonymous change in exon 8 of the gene for protein tyrosine phosphatase 1β (PTPN1). Invader assays were designed using the Invader Creator software (Hologic, Inc, Bedford, Mass., USA). Exemplary probe designs are listed in attached Table 1.

In this example, all assays may be designed to be run at the same incubation temperature (65° C. for biplex assays, 63° C. for monoplex assays) and may be performed in the integrated chamber as shown in FIG. 5. The probes of the biplex single nucleotide polymorphism (SNP) reaction may be the hairpin-like probes. In contrast, the probes of the monoplex single nucleotide polymorphism (SNP) reaction may be signal probes. The probes may be modified with a sulfhydryl (—SH) at 3' end and synthesized. To reduce potential space hindrance, a linker made of 10 nucleotide (nt) random oligomer may be added at the 3' end. Correspondingly, the sulfhydryl (—SH) group may be modified at the 3' end. These probes may be spotted with an aspirate-dispensing arrayer, like Biodot Arrayer (Cartesian Technologies, Irvine, Calif., USA) or similar contact-spotting arrayers. The probes may be immobilized on a modified glass slide with the sulfhydryl (—SH) group, and the glass with the immobilized probes array may be assembled with a plastic piece to form a chamber to form a reaction chamber or reactor.

Inside the reactor, a polymerase chain reaction (PCR) and single nucleotide polymorphism (SNP) assay reaction may be carried out simultaneously. A small quantity of purified genomic DNA may act as the template of the reaction. These templates may be added into the reaction chamber together with deoxyribonecleotide triphosphates (dNTP), polymerase chain reaction (PCR) primer, Taq polymerase, thermostable flap endonucleases (FEN), invader probes, optional signal probe (if a biplex assay is desired) and an appropriate buffer which can sustain the amplification and the single nucleotide polymorphism (SNP) reaction. The chamber is filled with the reaction fluid and sealed with a set of rubber plugs. The chamber is heated and cooled with a semi-conductor cooler to the temperatures required for the polymerase chain reaction (PCR) cycles. The polymerase chain reaction (PCR) may be performed in a standard process. The amplified nucleic acid products act as the templates of the single nucleotide polymorphism (SNP) reaction. In a typical biplex invader assay reaction system, reaction liquid is denatured for 5 minutes at 95° C. and incubated for 20 minutes at 65° C. In a typical monoplex invader assay reaction system, reaction liquid is denatured for 5 minutes at 95° C. and incubated for 20 minutes at 63° C.

TABLE 1

| SNP | Assay type | Oligonucleotide type | Sequence |
|---|---|---|---|
| CD36 | | Target sequence (allele 1) | 3'-GGTTACTAATCTGCTTAACTAAGAAAGACACTGAGTAGTCAAG*T**AAAGGACATTTTAAG TACAGAAC*-5' (SEQ ID NO: 1) |
| | | Target sequence (allele 2) | 3'-GGTTACTAATCTGCTTAACTAAGAAAGACACTGAGTAGTCAAGA*G**AAAGGACATTTTAAG TACAGAAC*-5' (SEQ ID NO: 2) |
| | Biplex | Invader | 5'-CCAATGATTAGACGAATTGATTCTTTCTGTGACTCATCAGTTCTT-3' (SEQ ID NO: 3) |
| | | Signal probe 1 | 5'-*TAAGGCGTCGGACAA*TTTCCTGTAAAATTCATGTCTTGC-3' (SEQ ID NO: 4) |
| | | Signal probe 2 | 5'-*GCGCCCAGGC*TTTCCTGTAAAATTCATGTCTTG-3' (SEQ ID NO: 5) |
| | | Hairpin-like probe 1 | SpSpSpSpSpSpSpSpSpSp-3'-*ATTCCGCAGCCTGTT*GAGCAGAGCCTTTTGGCTC(F)TG CTCA(Q)CAGTTG-5' (SEQ ID NO: 6) |
| | | Hairpin-like probe 2 | SpSpSpSpSpSpSpSpSp-3'-*CGCGGGTCCG*GAGCAGAGCCTTTTGGCTC(F)TGCTCC (Q)CAGTTG-5' (SEQ ID NO: 7) |
| | Monoplex | Invader | 5'-CCAATGATTAGACGAATTGATTCTTTCTGTGACTCATCAGTTCTT-3' (SEQ ID NO: 8) |
| | | Signal probe 1' | 5'-(Q)*CGCGCCGAGGA*TT(F)TCCTGTAAAATTCATGTCTTG-3'-SpSpSpSpSpSpSpSp SpSp (SEQ ID NO: 9) |
| | | Signal probe 2' | 5'-(Q)*CGCGCCGAGGC*TT(F)TCCTGTAAAATTCATGTCTTG-3'-SpSpSpSpSpSpSpSp SpSp (SEQ ID NO: 10) |
| PTP03 | | Target sequence (allele 1) | 3'-TGCTCCTGGACCTCGGGGTGGT*G**CTCGTATAGGGGGT*-5' (SEQ ID NO: 11) |
| | | Target sequence (allele 2) | 3'-TGCTCCTGGACCTCGGGGTGGT*A**CTCGTATAGGGGGT*-5' (SEQ ID NO: 12) |
| | Biplex | Invader | 5'-ACGAGGACCTGGAGCCCCCACCAT-3' (SEQ ID NO: 13) |
| | | Signal probe 3 | 5'-*ATGACGTGGCAGACC*GAGCATATCCCCCCA-3' (SEQ ID NO: 14) |
| | | Signal probe 4 | 5'-*CGCGCCGAGGT*GAGCATATCCCCCC-3' (SEQ ID NO: 15) |
| | | Hairpin-like probe 3 | SpSpSpSpSpSpSpSpSp-3'-*TACTGCACCGTCTGA*GAGCAGAGCCTTTTGGCTCTGCTC TTCGACT-5' (SEQ ID NO: 16) |
| | | Hairpin-like probe 4 | SpSpSpSpSpSpSpSpSp-3'-*GCGCGGCTCCA*GAGCAGAGCCTTTTGGCTCTGCTCTTCG ACT-5' (SEQ ID NO: 17) |
| | Monoplex | Invader | 5'-CGAGGACCTGGAGCCCCACCAT-3' (SEQ ID NO: 18) |
| | | Signal probe 3' | 5'-(Q)CGCGCCGAGG*C*GA(F)GCATATCCCCCCA-3'-SpSpSpSpSpSpSpSpSpSp (SEQ ID NO: 19) |
| | | Signal probe 4' | 5'-(Q)CGCGCCGAGG*T*GA(F)GCATATCCCCCA*C*-3'-SpSpSpSpSpSpSpSpSpSp (SEQ ID NO: 20) |

Legend:
Underlined type in each target sequence indicates the region complementary to the invader oligonucleotide.
Italic type indicates sequence complementary to the probe.
The bold underlined type indicates base is the site of the single nucleotide polymorphism (SNP).
The bold type indicates the part of the signal probe is the cleaved part.
The bold italic underlined type indicates the part of the hairpin-like probe is complementary to the cleaved part of the correspondong signal probe.
F = Fluorophore; Q = quencher; Sp = hexaethylene glycol spacer.

During the single nucleotide polymorphism (SNP) invader assay reaction, the signal probe 1 (1') is annealed to the CD36-allele 1. The resulting overlap with the invader oligonucleotide is recognized by a flap endonuclease (FEN) and the 5'-flap (marked in bold) is cleaved. In the monoplex reaction system, the quencher molecule of the signal probe 1' will be separated from the fluorophore molecule. The separated quencher diffuses away from the bound fluorophore. The bound fluorophore releases a fluorescent signal upon activation with light of an appropriate wavelength. In the biplex reaction system, the 5'-flap of the signal probe 1 complementary to its hairpin-like probe and the overlap with the hairpin terminal is recognized by the flap endonuclease (FEN), which will cleave the nucleotides separating the quencher molecule from the fluorophore molecule. The fluorophore may be excited by light of an appropriate wavelength to produce a fluorescence response. As described above, a part of signal probe sequence is complementary to the target sequence, and in the biplex assay, the other part of signal probe is complementary to the hairpin-like probe. As a result of the high sensitivity of the flap endonuclease (FEN) to recognize the overlap structure, the mismatch associated with the single nucleotide polymorphism (SNP) will not initiate the subsequent cleavage reaction that leads to a fluorescent response. When the single nucleotide polymorphism (SNP) assay reaction is complete, the fluorescent signal of the cleaved probes is excited by the laser and recorded by the charge-coupled device. The allele type of the single nucleotide polymorphism (SNP) may be analyzed by the signal strength of probes. Although the above discussion refers to a single nucleotide polymorphism (SNP) detection, one of skill in the art would readily recognize that this technology may be expanded for multiple single nucleotide polymorphism (SNP) detection. Theoretically, for each single nucleotide polymorphism (SNP) site, a set of signal probe, invasive probe, and hairpin-like probe (for biplex reaction) may be prepared and used with one microchip.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety.

What is claimed is:

1. A method for detecting a single nucleotide polymorphism in a target nucleic acid comprising:
   (a) providing (i) a linear or two-dimensional microarray of discrete regions, each having a defined area, formed on an upper surface of a solid support, each region of the microarray comprising a signal probe and an invader probe, wherein the signal probe or the signal and the invader probe are immobilized on the upper surface, and (ii) a plurality of different samples having an amplified target nucleic acid suspected of having a single polynucleotide polymorphism at discrete regions in the microarray,
   wherein the invader probe comprises sequences selected to anneal to a single-strand of the amplified target nucleic acid 5' to the single polynucleotide polymorphism and a 3' most nucleotide that does not anneal to the single polynucleotide polymorphism, wherein the signal probe comprises a fluorescent label linked to sequences selected to not anneal to the single-strand of the amplified target nucleic acid or to the invader probe linked to sequences selected to anneal to the target nucleic acid with a single nucleotide polymorphism, wherein the signal probe further comprises a fluorescence quencher linked to the sequences selected to anneal to the single-strand of the amplified target nucleic acid;
   (b) annealing at each discrete region in the microarray the invader probe and the signal probe to the single-strand of the amplified target nucleic acid suspected of having a single polynucleotide polymorphism to provide a sample complex;
   (c) contacting the sample complex with a flap endonuclease to activate a fluorescence response; wherein if the signal probe anneals to the single-strand of the amplified target nucleic acid at a single polymorphic nucleotide, the flap endonuclease cleaves the signal probe 3' to the single polymorphic nucleotide producing a cleaved 5' flap sequence that produces the fluorescent response; and
   (d) detecting the fluorescence response in the discrete regions, wherein fluorescence in a discrete region is indicative of the presence of the single nucleotide polymorphism in the sample.

2. The quantitative method of claim 1, wherein the providing an amplified target nucleic acid suspected of having a single polynucleotide polymorphism comprises:
   (i) denaturing the target nucleic acid to provide a pair of single-stranded target nucleic acids;
   (ii) annealing a primer to the each single-stranded target nucleic acid; and
   (iii) extending each primer annealed to each single-stranded target nucleic acid to provide an amplified target nucleic acid.

3. The quantitative method of claim 1, further comprising analyzing the fluorescence response.

4. A method for detecting a single nucleotide polymorphism in a target nucleic acid comprising:
   (a) providing (i) a linear or two-dimensional microarray of discrete regions, each having a defined area, formed on an upper surface of a solid support, each region of the microarray comprising a hairpin probe immobilized on the upper surface, (ii) a plurality of different samples having an amplified target nucleic acid suspected of having a single polynucleotide polymorphism at discrete regions in the microarray, (iii) a signal probe and (iv) an invader probe,
   wherein the invader probe comprises sequences selected to anneal to the single-strand of the amplified target nucleic acid 5' to the single polynucleotide polymorphism and a 3' most nucleotide that does not anneal to the single polynucleotide polymorphism, wherein the signal probe comprises sequences selected to not anneal to the single-strand of the amplified target nucleic acid or to the invader probe linked to sequences selected to anneal to the target nucleic acid with a single nucleotide polymorphism, wherein the hairpin probe comprises sequences selected to anneal to the sequences in the signal probe selected to not anneal to the single-strand of the amplified target nucleic acid and to the nucleotide that is the single nucleotide polymorphism, and wherein the hairpin probe comprises a fluorescence quencher 5' to the single nucleotide polymorphism and a fluorescent label 3' to the single nucleotide polymorphism;

(b) annealing at each discrete region in the microarray the invader probe and the signal probe to the single-strand of the amplified target nucleic acid suspected of having a single polynucleotide polymorphism to provide a sample complex;

(c) contacting the sample complex with a flap endonuclease to provide a mixture, wherein if the signal probe anneals to single-strand of the amplified target nucleic acid at a single polymorphic nucleotide, the flap endonuclease cleaves the signal probe 3' to the single polymorphic nucleotide to provide the 5' flap sequence;

(d) subjecting the mixture to conditions that allow for annealing the 5' flap sequence to the hairpin probe;

(e) contacting the mixture in (d) with a flap endonuclease; and (f) detecting the fluorescence response in the discrete regions, wherein fluorescence in a discrete region is indicative of the presence of the single nucleotide polymorphism in the sample.

5. The quantitative method of claim 4, wherein the providing an amplified target nucleic acid suspected of having a single polynucleotide polymorphism comprises:

(i) denaturing the target nucleic acid to provide a pair of single-stranded target nucleic acids;

(ii) annealing a primer to the each single-stranded target nucleic acid; and (iii) extending each primer annealed to each single-stranded target nucleic acid to provide an amplified target nucleic acid.

6. The quantitative method of claim 4, further comprising analyzing the fluorescence response.

7. The quantitative method of claim 4, wherein the probe is printed and immobilized onto the substrate using a microarray printer.

8. The quantitative method of claim 4, wherein the substrate comprises silicon, glass, quartz, a ceramic, a rubber, a metal, a polymer, a hybridization membrane, or a combination thereof.

9. The quantitative method of claim 4, wherein the substrate is chemically modified with a reagent selected from a silane, avidin, poly-L-lysine, streptavidin, a polysaccharide, a mercaptan, or a combination thereof.

10. The quantitative method of claim 4, wherein the probe comprises a linker with a sulfhydryl (RSH), amino ($NH_2$), hydroxyl (OH), carboxaldehyde (CHO), or carboxylic acid (COOH) group at the 3' end.

11. The quantitative method of claim 10, wherein the linker comprises about a ten nucleotide random oligomer.

12. The quantitative method of claim 10, wherein the probe is immobilized onto a silanized glass substrate with the sulfhydryl (RSH) group at the 3' end.

* * * * *

```
                        SEQUENCE LISTING

<160> NUMBER OF SEQ ID NOS: 20

<210> SEQ ID NO 1
<211> LENGTH: 68
<212> TYPE: DNA
<213> ORGANISM: Artificial Sequence
<220> FEATURE:
<223> OTHER INFORMATION: A synthetic oligonucleotide

<400> SEQUENCE: 1
caagacatga attttacagg aaatagaact gatgagtcac agaaagaatc aattcgtcta      60
atcattgg                                                              68

<210> SEQ ID NO 2
<211> LENGTH: 68
<212> TYPE: DNA
<213> ORGANISM: Artificial Sequence
<220> FEATURE:
<223> OTHER INFORMATION: A synthetic oligonucleotide

<400> SEQUENCE: 2
caagacatga attttacagg aaagagaact gatgagtcac agaaagaatc aattcgtcta      60
atcattgg                                                              68

<210> SEQ ID NO 3
<211> LENGTH: 45
<212> TYPE: DNA
<213> ORGANISM: Artificial Sequence
<220> FEATURE:
<223> OTHER INFORMATION: A synthetic oligonucleotide

<400> SEQUENCE: 3
ccaatgatta gacgaattga ttctttctgt gactcatcag ttctt                     45

<210> SEQ ID NO 4
<211> LENGTH: 39
<212> TYPE: DNA
<213> ORGANISM: Artificial Sequence
<220> FEATURE:
<223> OTHER INFORMATION: A synthetic oligonucleotide
```

<400> SEQUENCE: 4
taaggcgtcg gacaatttcc tgtaaaattc atgtcttgc                    39

<210> SEQ ID NO 5
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 5
gcgcccaggg ctttcctgta aaattcatgt cttg                         34

<210> SEQ ID NO 6
<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 6
gttgacactc gtctcggttt tccgagacga gttgtccgac gcctta            46

<210> SEQ ID NO 7
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 7
gttgaccctc gtctcggttt tccgagacga ggccctgggc gc                42

<210> SEQ ID NO 8
<211> LENGTH: 45
<212> TYPE: DNA
<213> ORGANISM: Artificial Sequence
<220> FEATURE:
<223> OTHER INFORMATION: A synthetic oligonucleotide

<400> SEQUENCE: 8
ccaatgatta gacgaattga ttctttctgt gactcatcag ttctt             45

<210> SEQ ID NO 9
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 9
cgcgccgagg atttcctgta aaattcatgt cttg                         34

<210> SEQ ID NO 10
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 10
cgcgccgagg ctttcctgta aaattcatgt cttg                         34

<210> SEQ ID NO 11
<211> LENGTH: 39
<212> TYPE: DNA

```
<213> ORGANISM: Artificial Sequence
<220> FEATURE:
<223> OTHER INFORMATION: A synthetic oligonucleotide

<400> SEQUENCE: 11 tgggggata tgctcgtggt gggggctcca ggtcctcgt                    39

<210> SEQ ID NO 12
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 12 tgggggata tgctcatggt gggggctcca ggtcctcgt                    39

<210> SEQ ID NO 13
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 13
acgaggacct ggagccccca ccat                                   24

<210> SEQ ID NO 14
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 14
atgacgtggc agaccgagca tatccccca                              30

<210> SEQ ID NO 15
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 15
cgcgccgagg tgagcatatc ccccc                                  25

<210> SEQ ID NO 16
<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 16
tcagcttctc gtctcggttt tccgagacga gagtctgcca cgtcat            46

<210> SEQ ID NO 17
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 17
tcagcttctc gtctcggttt tccgagacga gacctcggcg cg                42
```

```
<210> SEQ ID NO 18
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 18
cgaggacctg gagcccccac cat                                              23

<210> SEQ ID NO 19
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 19
cgcgccgagg cgagcatatc cccca                                            26

<210> SEQ ID NO 20
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 20
cgcgccgagg tgagcatatc cccccac                                          27
```